Figure 1:
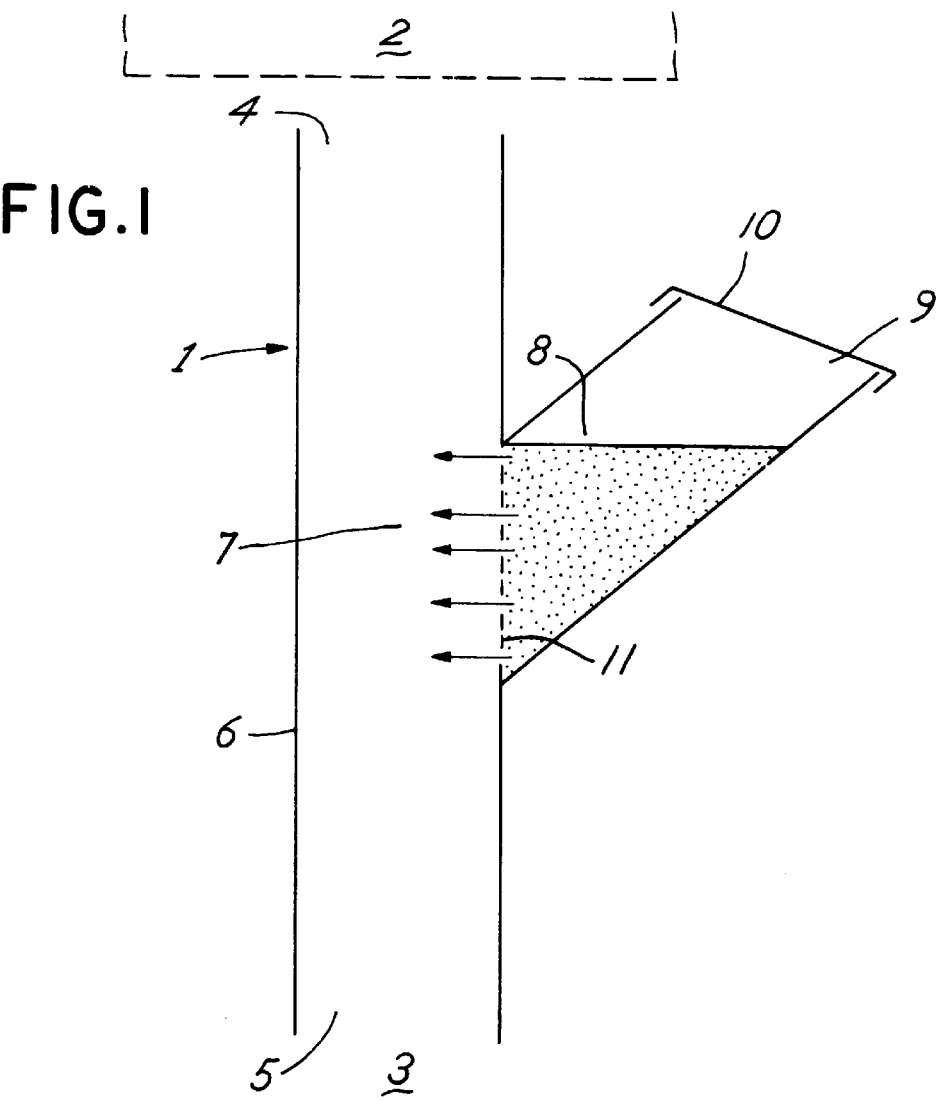

United States Patent [19]
Wilson et al.

[11] Patent Number: 5,858,793
[45] Date of Patent: *Jan. 12, 1999

[54] STERILE OR SPECIFIC PATHOGEN FREE ENVIRONMENT PRODUCTS

[75] Inventors: Michael Wilson, Cambridgeshire; Philip Monro, Southhampton, both of Great Britain

[73] Assignee: Hampshire Advisory and Technical Services Limited, Southhampton, England

[*] Notice: The term of this patent shall not extend beyond the expiration date of Pat. No. 5,610,070.

[21] Appl. No.: 741,314

[22] Filed: Oct. 30, 1996

Related U.S. Application Data

[62] Division of Ser. No. 237,719, Apr. 29, 1994, Pat. No. 5,610,070, which is a continuation of Ser. No. 940,969, Nov. 5, 1992, abandoned.

[51] Int. Cl.⁶ .................................................. G01N 33/48
[52] U.S. Cl. ........................... 436/63; 210/650; 210/295; 210/651; 435/420; 435/800; 435/962; 436/178; 436/514; 47/60; 47/62; 119/260
[58] Field of Search ............................. 436/63, 514, 175, 436/178; 210/650, 295, 649, 651; 435/325, 800, 962, 420; 47/59, 60, 61, 62, 58; 119/245, 259, 260; 604/82, 83, 92, 283, 905

[56] References Cited

U.S. PATENT DOCUMENTS

| | | | |
|---|---|---|---|
| 2,672,432 | 3/1954 | Goetz | 195/139 |
| 2,677,646 | 5/1954 | Lovell et al. | 195/139 |
| 2,761,813 | 9/1956 | Goetz | 195/80 |
| 3,096,148 | 7/1963 | Walker | 21/58 |
| 3,697,222 | 10/1972 | Sierra | 21/54 A |
| 4,296,205 | 10/1981 | Verma | 435/240 |
| 4,421,849 | 12/1983 | Breuker | 435/32 |
| 4,424,056 | 1/1984 | Urquhart et al. | 604/56 |
| 4,485,171 | 11/1984 | Ikeda et al. | 435/30 |
| 4,654,197 | 3/1987 | Lilja et al. | 422/56 |
| 4,661,100 | 4/1987 | Rechsteiner | 604/327 |
| 4,746,489 | 5/1988 | Arnold | 422/29 |
| 4,839,296 | 6/1989 | Kennedy et al. | 436/170 |
| 4,867,876 | 9/1989 | Kopf | 210/228 |
| 4,908,315 | 3/1990 | Kertz | 435/240.4 |
| 4,920,105 | 4/1990 | Zelman | 514/59 |
| 5,223,428 | 6/1993 | Rose | 435/240 |
| 5,610,070 | 3/1997 | Wilson et al. | 436/63 |

FOREIGN PATENT DOCUMENTS

| | | |
|---|---|---|
| 82173/87 | 12/1986 | Australia . |
| 0024048 | 8/1980 | European Pat. Off. . |
| 0343357 | 11/1989 | European Pat. Off. . |
| 0379788 | 11/1989 | European Pat. Off. . |
| 2514366 | 4/1983 | France . |
| 2656331 | 12/1989 | France . |
| 839245 | 5/1952 | Germany . |
| 5115570 | 5/1988 | Japan . |
| 864732 | 4/1961 | United Kingdom . |
| 2001755 | 2/1979 | United Kingdom . |
| 2150849 | 7/1985 | United Kingdom . |
| 80/02805 | 12/1980 | WIPO . |
| 88/10103 | 12/1988 | WIPO . |
| 89/05167 | 6/1989 | WIPO . |
| 90/02580 | 3/1990 | WIPO . |
| 90/09200 | 8/1990 | WIPO . |

OTHER PUBLICATIONS

Millipore Corporation, Bedford, MA USA, Catalogue 1994–1995, pp. 389–391, 279, 293, Nov. 1993.
Daigger & Company, Inc., Catalog 1996, pp. 161–162.
Daigger & Company, Inc., Catalog 1996, pp. 127–128, 161–162.

*Primary Examiner*—Lorraine Spector
*Assistant Examiner*—Eliane Lazar-Wesley
*Attorney, Agent, or Firm*—Banner & Witcoff Ltd.

[57] ABSTRACT

Methods of maintaining or providing sterile or specific pathogen free environments are disclosed. The methods involve the use of semi-permeable membrane materials between the sterile or pathogen free environment and surrounding potentially hostile environments.

15 Claims, 1 Drawing Sheet

STERILE OR SPECIFIC PATHOGEN FREE ENVIRONMENT PRODUCTS

This is a divisional of application Ser. No. 08/237,719 filed Apr. 29, 1994 (now U.S. Pat. No. 5,610,070) which is a continuation of application Ser. No. 07/940,969 filed Nov. 5, 1992 (abandoned).

The present invention relates to sterile environment products and more particularly but not exclusively to such products for use in medical, horticultural, industrial, agricultural and like establishments in which a specific pathogen free (SPF) environment is required.

For the avoidance of doubt, the term Specific Pathogen Free (herein abbreviated to SPF) shall include environment free not only of specific pathogens but also of specific toxins and toxic substances having molecular weight above the specific exclusion point (cut-off point) of certain semi-permeable membranes referenced hereinafter.

In our co-pending PCT patent application number PCT/GB/89/01119 (publication number WO/90/03333) there is disclosed a water purifying system for providing non-toxic solutions of water-soluble solids from water sources which may contain undesirable micro-organisms.

The present invention seeks to apply similar principles to those discussed in the above application for the purposes of simplifying certain medical and industrial procedures and improving availability of drugs where limited storage or other space is available or where such drugs in solution may become unstable. The invention may also contribute to reducing costs of distribution and supply in sterile form.

The invention also seeks to provide improved procedures for use in horticulture, fisheries (including establishments breeding and/or rearing other aquatic or marine lifeforms), and the like and to provide improvements in in-vitro and cell culture systems including tissue culture and organ culture for example.

All of the above mentioned systems have one principal difficulty which is to maintain sterility in the solution or environment while introducing secondary soluble substance or substances such as drugs or nutrients to that solution and maintaining an SPF environment.

It is one object of the present invention to provide a method and equipment for alleviating this difficulty.

According to one aspect of the present invention there is provided a method of introducing a secondary substance into a liquid SPF environment comprising the steps of interfacing the SPF environment with a surrounding environment by means of a semi-permeable membrane and introducing said secondary substance on an opposed side of the membrane to the SPF environment whereby the secondary substance(s) may pass through the membrane into the SPF environment while contaminants of higher molecular weight are excluded.

For the avoidance of doubt the term contaminant of higher molecular weight includes micro-organisms and soluble toxic substances.

According to another aspect of the present invention there is provided an in-line connector for use with (e.g.) drip-sets, the connector comprising a first port for connection to a source of sterile liquid, a second port for connection to a transfer tube or injection module and a third port through which secondary substances may be introduced, said first and second ports being connected to said third port by way of a semi-permeable membrane whereby drugs and/or nutritional solutes may be introduced to solution in a transfusing liquid without introducing external contaminants.

According to a further aspect of the present invention there is provided a method of in-vitro culture comprising the steps of enclosing cell(s) to be cultured in a sealable receptacle which has at least a portion comprising a semi-permeable membrane and contacting an external surface of the semi-permeable membrane with a solution containing nutrients or other secondary substances for treatment of the culture whereby such nutrients or secondary substances may pass into the culture solution without contaminants of higher molecular weight being introduced thereto.

Figure 2:
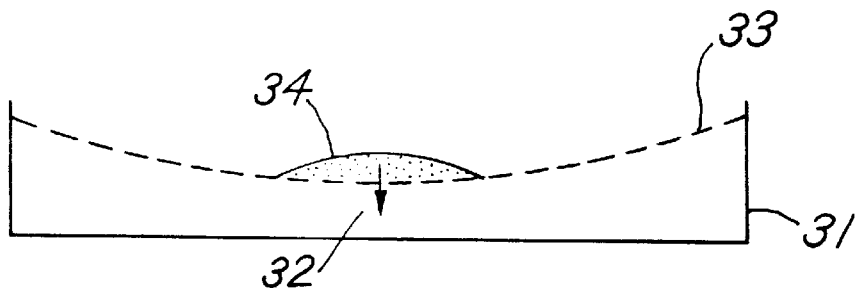

The present invention will now be described by way of example only with reference to the accompanying drawings of which:

FIG. 1 is a schematic diagram of a drip set including a connector in accordance with the present invention; and FIG. 2 shows a cell culture system in accordance with the invention.

Reference to the specification of PCT patent application number PCT/GB/89/01119 will show the kind of contaminants which may be excluded from solutions by use of semi-permeable membranes of different types. Such contaminants include (but are not limited to) microbial pathogens and other micro-organisms, microbial spores and cysts and the like including the exclusion of specific cell or tissue types.

It will be appreciated that while the invention of the cited specification is directed to providing solutions having improved sterility from water which may be severely contaminated, the principle of reducing disease or contamination risks is necessary in other environments.

For example, it is often desirable to introduce one or more drugs into a patient (whether human or animal) by way of a drip set. Unless each drug and combination of drugs likely to be of use are stored in packs ready for use, some delay may occur in obtaining suitable sterile supplies. Further, as is well known, certain drugs deteriorate during storage and certain combinations of drugs in solution may over a period of time inter-react and become ineffective.

Although the term drip set is used herein (as a reference to intravenous infusion sets) and drip sets are referred to throughout the specification, the invention is not limited to drip sets per se and it will be appreciated that the use of the invention extends to for example naso-gastric feeding tubes, perfusion solutions and the like.

Thus, referring to FIG. 1, we provide a connector 1 for insertion in line between a sterile (saline) solution pack 2 and a feeder tube 3. The pack 2 is of standard form and will have been prepared under sterile conditions and may have undergone subsequent sterilisation processes such as by irradiation for example.

The connector 1 comprises a first connector port 4 for connection to the outlet of the pack 2 and a second connector port 5 for connection to the feeder tube. The body 6 of the connector 1 is of translucent plastics material and serves to provide visibility of the drip flow.

The ports 3 and 4 form a part of a first chamber 7 which is separated from a second chamber 8 by means of a semi-permeable membrane 11 of known material (for example Visking (trademark) membrane) in the wall of the body 6. The second chamber 8 has an inlet port 9 which may be capped by a plug 10 as shown in the drawing. In use, the drip set is assembled in traditional manner connecting the pack 2 outlet by way of the connector I to a feeder tube and injection device for introducing the solution to a patient. Additive drugs may now be introduced through the inlet port 9. The drug introduced into the inlet port 9 may now diffuse through the membrane 11 into the drip solution and thence to the patient.

While it will be realised that as far as practicable, substances introduced to the chamber 8 should be sterile and preferably handled aseptically, the semi-permeable membrane 11 will ensure that sterility of liquids held in the pack 2 is maintained.

Although as thus far described, it is assumed that the contents of the pack 2 are a saline solution, it will be appreciated that other solutions may be used. However, the ability to introduce drugs of differing kinds into appropriate isotonic or standard infusions such as saline solution or dextran solution at the point of administration has several benefits.

Firstly, it is unnecessary to hold in store large quantities of premixed drugs in sterile solution since each drug or combination of drugs may be held in a stable form which is not necessarily in sterile condition. Quantities of sterile infusion solutions only need be held. Thus storage, transportation and deterioration costs may be reduced.

Further, where unusual combinations of drugs are required these can be provided without time wastage in obtaining supplies specially prepared in sterile conditions.

Yet another advantage is noted in that regardless of environmental hostility, provided that the primary injection fluid is sterile ab initio, introduction of further substances to that solution may occur without introduction of pathogens from the environment.

It will also be realised that there is a reduction of risk to persons administering drug combinations to patients infected with dangerous pathogens since the need to open a line is reduced thus the chances of such persons coming into contact with infected body fluids is correspondingly reduced.

Where the primary requirement is for protection of administering persons, the semi permeable membrane may be selected to have a cut-off point slightly below the molecular weight of the infecting organism/virus whereby treatment substances of only slightly lower molecular weight than the infecting organism may be used.

In an alternative method of using the connector 1, in circumstances where a drug combination is most effective when mixed at the last possible moment, the inlet port 9 may be replaced by a connector (not shown) to which a second pack containing a predetermined different solution may be connected. Thus by providing the connector in the form shown, intermixing of drugs may occur temporally close to the time of administration thus avoiding possible adverse inter reaction of drug combinations.

It will also be appreciated that the system may be employed to add specific drugs or additives prior to administration.

A further benefit of the present invention will be appreciated where slow continuous administration of (e.g.) drugs would be beneficial to the patient. In such cases, a coated dry drug may be added at the port 9 so that the combination of the coating and slow membrane passage restricts the rate at which the drug is administered. The same result may be achieved by selecting a membrane or composite membrane to have a specifically slow transfer rate, possibly by restricting the surface area of the membrane for example. In a further alternative, a plurality of membranes separated by a short distance may be employed so that cumulative transfer rates reduce the rate of drug infusion.

A further adaptation for use independently or in combination with the above utilises selective ion membranes and/or selective ion powders to ensure the exclusion of specific chemical groups (for example sodium ions).

The progress hereinbefore described and other aspects of the invention as hereinafter described may be used in industrial applications where substances may be introduced to a sealed liquid container without introduction of unwanted foreign substances of higher molecular weight. In industrial situations it will be appreciated that the substance to which other substances are introduced may be (e.g.) a solvent or other liquid as an alternative to the sterile water/saline solution used in medicinal applications.

It will be appreciated that while as herein described, saline solutions and drug solutions have been specifically mentioned, the invention may be applied equally to other solutions in common usage including distilled water and may be used with blood and blood substitutes.

In a further development of the system, particularly to reduce risk to carers when dealing with patients infected with dangerous pathogens, a permanent "injection" point may be provided for insertion for example into a vein in the patients wrist. It is now common to provide an injection point in medium to long term patients in hospitals by inserting a needle attached to a short tube which is capped. The device is then strapped to the patient providing a connection point for an outlet from a syringe without necessitating the use of further needles and thus reducing discomfort to the patient from a large number of injection sites. This modification may be applied to the form of device sometimes referred to as a "Butterfly".

The present invention provides a similar arrangement comprising a needle attached to a small chamber, the tube of the needle being linked to the pot by way of a semi permeable membrane. Thus, the possibility of an infected patients blood leaking back through the connection port is significantly reduced.

It will be appreciated that the port 9 may have a control mechanism below the membrane whereby transfer of substances through the membrane to the chamber 7 thereby permitting additive drug dosages for example to be commenced and stopped as necessary.

Turning now to FIG. 2, the invention may find use in in-vitro culture systems, tissue culture systems and organ culture systems (including plant, animal and bacterial culture systems) where it is desired to culture cells in sterile conditions but where additional substances such as nutrients of differing kinds are required to be introduced.

Additional substances as referred to above may include (but are not limited to) hormones, growth factors, mineral substances, gases and insecticides or fungicides.

In this case, the initial cell or cells to be cultured are introduced into a sealable package which has been previously sterilised, the introduction being carried out in as near sterile conditions as possible. An initial supply of nutrient solution may be introduced to the package concurrently or may previously have been packaged within, prior to sterilisation for example by irradiation.

The package has at least one section comprising a semi-permeable membrane such that by placing the package in a solution of higher concentration than the nutrient solution contained within, nutrients may pass through the membrane into the culture.

As nutrients are taken up in the culture, the package may be placed in nutrient solution so that nutrients from the solution may be added to the culture without further introducing undesirable contaminants such as bacteria. It will of course be realised that substances other than nutrients may be introduced using this method provided that such substances are of lower molecular weight than the cut-off point of the membrane.

In a specific alternative to an immersible package, referring specifically to FIG. 2, a culture dish 31 containing a sterile nutrient solution 32 to which a cell or cells to be cultured have been added is capped by a semi-permeable membrane 33. Fresh nutrients 34 (or drug treatments and other substances) in solution are added above the membrane 33 as required and permeate through the membrane to the solution 32 thereby maintaining or modifying the balance of nutritional or other concentration therein. Substances of lower molecular weight than the cut-off point of the membrane 33, for example excreta whose removal may benefit the culture, may diffuse out of the culture medium in the same manner. Such substances include Urea and gaseous materials such as armnonia.

Higher molecular weight substances (including the cell or cells under culture) are retained within the culture dish 31 by the membrane 33. Thus as with the drug/nutrient administration system of FIG. 1 hereinbefore described the culture medium 32 retains its sterility regardless of the hostility of the surrounding environment and/or the nature and sterility of secondary substances being introduced.

It will be appreciated that gases in solution or in gaseous state may be diffused through the semi-permeable membrane materials and such gases are included within the term secondary substances. Both removal and introduction of such gases is possible where the culture might be beneficially so treated.

This method of protection of cell cultures may also be applied in a similar way to facilitate the propagation of plants in sterile conditions.

For example using tissue culture to reproduce plants from small sections taken from a healthy parent, new plants may be grown inside a SPF environment while nutritional elements can still be added and organisms (including insects, fungal spores and the like) are excluded.

In a further development of the plant culture system, seeds may be encapsulated in a semi permeable membrane bag or the roots of seedlings may be encapsulated such that the further development of plants therefrom may proceed without interference from certain adverse infectious agents such as fungi or bacteria present in soils affecting young tissue.

Specific nutrients or symbiotic organisms may be encapsulated around the root system or seed to ensure clean, rapid development of the young plant and specific helpful bacteria may also be introduced. For example, encapsulating cellulolytic bacteria which can "feed" on the cellulose merfibrane while fixing nitrogen can improve the growth rate of the young plants by ensuring a ready supply of nitrogenous compounds. Such bacteria will over a predetermined period also dissolve the surrounding membrane when the plant is sufficiently developed.

Examples of cellulolytic bacteria which could perform this function are reported in an article in "Science", Volume 242 at page 1157.

Other uses for SPF environments provided by use of semi-permeable membranes can be shown to include for example fish farming where fungal infection is a possible danger. Thus by providing an environment which is known to be initially free of specific pathogens and organisms (for example in a plastics enclosure which isolates the SPF environment from the surrounding environment) and providing an interface between the SPF environment and the surrounding environment which comprises one or more semi-permeable membranes it is possible to maintain substantially SPF.

The environment would normally be water for example into which nutrients may be introduced, the nutrients then passing into the environment while contaminants are effectively excluded. Waste products of low molecular weight may also diffuse from the enclosure into the surrounding environment.

For example fish held within an individual environment may be prevented from damage by contaminating organisms and fungal infections.

The method may also be of use in similar environments where undesirable organisms may adversely affect the survival chances of the end animal product. For example, not only fish per se but also fish eggs and other larval forms may benefit from protection at an early stage in their life cycles.

Further, crustacea including small crabs, prawns and the like and other invertebrates may be reared in a protected environment even if only in very early stages.

In order to demonstrate the efficacy of the invention, the following test has been carried out. 10 mL of phenol red solution placed in a measuring cylinder and a sample taken for absorption at 550 nm. 10 mL water placed inside a six inch length of dialysis tubing having a diameter of 1.6 cm which was then sealed and immersed in the phenol red held in the measuring cylinder.

Samples were taken from the measuring cylinder and from the dialysis tubing and the absorbance at 550 nm determined after appropriate dilution. The results are given in the following table:

| | Absorbance at 550 nm | |
|---|---|---|
| Time (h) | Inside tubing | Outside tubing |
| 0 | 0 | 2.57 |
| 0.5 | 0.19 | 2.59 |
| 0.75 | 0.32 | 2.60 |
| 1.75 | 0.56 | 2.32 |
| 3.25 | 0.92 | 2.19 |
| 6.0 | 1.49 | 2.11 |
| 24.0 | 1.96 | 2.05 |

Phenol red has a molecular weight of 354 whereas the molecular weight cut-off of the tubing used was 12,000. The test therefore shows that this low molecular weight substance can penetrate into the dialysis tubing, equilibrium being reached after between 6 and 24 hours. Earlier tests reported in the referenced pending PCT patent Application have shown that bacteria, viruses and other organisms cannot penetrate such tubing. Accordingly the test demonstrates that low molecular weight substances may be added aseptically to a solution contained within dialysis tubing without actually breaking the seal of such tubing.

A further aspect of the invention provides protection for operatives involved in the testing and identification of potentially toxic substances.

The safe handling of potentially infectious biological tissues and fluids by personnel who have to test these materials may be improved by use of the methods of the present invention. To provide protection to such personnel, fluid samples or tissue samples are collected into a container comprising at least in part a membrane having an appropriate cut-off selected to retain the sample.

The container may have a fixed known volume enabling quantitative analysis to be carried out. Substances of interest which are the subject of these tests but not micro-organisms will be below the selected molecular weight cut off of the membrane and can therefore diffuse through the membrane. Test reagents may also be below the molecular weight cut off of the membrane.

Analysis can be carried out by way of the following examples:

The container may be in direct contact with the desired test reagent and the test result directly read. For example faecal material for test for occult blood may be contained within the sealed container. Contacting the membrane with a test reagent allows the reagent to pass into the container to react with occult blood present thereby indicating the presence or absence of same. The operative is protected from any harmful pathogens within the faecal material which are prevented from passing through the membrane material.

A further benefit of this kind of testing may also be apparent in that several containers may be placed in a common solution of reagent without risk of cross contamination of samples.

Alternatively, the container may be immersed in a known volume of liquid reagent and after a pre-determined period of time allowing substances to diffuse into the liquid, testing may be completed without risk to the operator. Example suitable for this kind of testing include the testing of blood or urine for the presence of electrolytes such as potassium or sodium. Similarly, sugar in urine tests may be carried out either qualitatively or quantitatively. Visual assessment of test results will be possible in many cases particularly if the test reagent is applied directly to the outside of the membrane.

Results can be achieved by test substances diffusing into the package or into the sealed chamber, the container including a transparent or translucent section to allow visual inspection of (e.g) colour changes.

In a further use of the invention, enclosing objects to be disinfected inside a sealed container either partially or totally comprised of semi-permeable membrane material and including a disinfectant solute, permits disinfection even if doubts exist as to the sterility of the solution to be used in the disinfection process.

Thus, contacting the membrane material with a solution (e.g) water causes the solute to be dissolved to commence disinfection, and reduces the need for disinfectant solutions to be held and stored in quantity for long periods.

Examples of objects which may be so sterilised include contact lenses which may be enclosed in a sealable package and left in solution overnight. Sterile saline solution for washing of the disinfecting object may be prepared at the same time by use of a second package which may be linked to the first package in such a way as to permit the lens to be transferred to the saline solution without further handling.

A similar principle may be applied in maintaining or reinforcing the sterility of instruments to be used in operating theatres whereby the instrument may be enclosed 3.n a package with a solute, the package being of semi-permeable membrane material. Standard radiation methods of providing primary sterilisation may be used. However, prior to use of the instrument, the package may be placed in water in case the packaging has been damaged in transit.

In this case a sterility check may be carried out by adding a high molecular weight dye, for example blue dextran, to the water so that any colour presence inside the sterile package indicates possible contamination.

We claim:

1. A method of testing a potentially infectious substance selected from the group consisting of blood, tissue, and other biological samples, said method comprising the steps of:
   (a) placing the potentially infectious substance to be tested in a container of which at least a part of the container is formed of a semi-permeable membrane, the semi-permeable membrane having a molecular weight cut-off such that viruses and other potentially infectious organisms are retained within the container by virtue of having a molecular weight higher than the molecular weight cut-off;
   (b) closing the container; and
   (c) contacting the semi-permeable membrane with at least one reagent solution thereby allowing non-infectious components of said substance to pass through the membrane and react with the reagent solution, therefore allowing the test to be performed.

2. A method of testing as claimed in claim 1 further characterized by said container containing a predetermined volume of a substance to be tested, said substance being in contact via the semi-permeable membrane with a predetermined volume of said reagent solution.

3. A method of testing as claimed in claim 1 further characterized in that a plurality of said containers are tested in a common solution of test reagent, whereby a plurality of substances may be simultaneously tested without risk of cross contamination.

4. A method of testing a potentially infectious substance selected from the group consisting of blood, tissue, and other biological samples, said method comprising the steps of:
   (a) placing the potentially infectious substance to be tested in a container of which at least a part of the container is formed of a semi-permeable membrane, the semi-permeable membrane having a molecular weight cut-off such that viruses and other potentially infectious organisms and toxins thereof are retained within the container by virtue of having a molecular weight higher than the molecular weight cut-off;
   (b) closing the container; and
   (c) contacting the semi-permeable membrane with at least one reagent solution thereby allowing non-infectious and non-toxic components of said substance to pass through the membrane and react with the reagent solution, therefore allowing the test to be performed.

5. A method of testing as claimed in claim 4 further characterized by said container containing a predetermined volume of a substance to be tested, said substance being in contact via the semi-permeable membrane with a predetermined volume of said reagent solution.

6. A method of testing as claimed in claim 4 further characterized in that a plurality of said containers are tested in a common solution of test reagent, whereby a plurality of substances may be simultaneously tested without risk of cross contamination.

7. A method of introducing a secondary substance in solution into a liquid specific pathogen free (SPF) environment, said SPF environment containing living tissue selected from the group consisting of plant seeds, plant seedlings, plant cuttings, plants, root system of plant seedlings, root systems of plant cuttings, root systems of plants, fish eggs, larval forms of fish and fish, said method comprising the steps of interfacing the SPF environment with a surrounding environment by means of a semi-permeable membrane and introducing said solution on an opposed side of the membrane to the SPF environment whereby the secondary substance in solution may pass through the membrane into the SPF environment while contaminants of higher molecular weight are excluded.

8. A method of treating an in-vitro culture comprising the steps of enclosing cell(s) to be cultured in a sealable receptacle which has at least a portion comprising a semi-permeable membrane, said membrane having a molecular weight cut off such that viruses and other potentially infectious organisms are unable to pass through the membrane, sealing said receptacle, and contacting an external surface of the semi-permeable membrane with a solution containing nutrients or other secondary substances for treatment of the culture whereby such nutrients or secondary substances may pass into the culture solution without contaminants of higher molecular weight being introduced thereto, and whereby said semi-permeable membrane provides the only means for introducing nutrients or secondary substances into the culture.

9. An in-line connector for use with drip-sets, the connector comprising a first port for connection to a source of sterile liquid, a second port for connection to a transfer tube or injection module and a third port through which secondary substances may be introduced, said first and second ports being connected to said third port by way of a semi-permeable membrane whereby drugs and/or nutritional solutes may be introduced to the solution in a transfusing liquid without introducing external contaminants.

10. An in-line connector as claimed in claim 8 further characterized in that the membrane is selected to restrict the rate of flow of the secondary substance whereby the rate of transfer of the secondary substance to the transfusing liquid is controlled.

11. An in-line connector as claimed in claim 9 further characterized in that a second semi-permeable membrane spatially separated from the first said membrane is provided whereby the rate of flow of the secondary substance is restricted whereby the rate of transfer of the secondary substance to the transfusing liquid is controlled.

12. An in-line connector as claimed in claim 9 characterized in that the first and second ports are connected to a first chamber and the third port is connected to a second chamber, the first and second chambers being connected by the semi permeable membrane.

13. An in-line connector as claimed in claim 12 further characterized in that at least the first chamber is of translucent material whereby the rate of flow of the transfusing liquid is visible.

14. A method of disinfecting objects comprising inserting the object in a sealable package at least partially formed of semi-permeable membrane material, enclosing a disinfectant solute within the package, sealing the package and contacting the semi-permeable membrane with a solution whereby the solution enters the package to effect disinfection while contaminants of higher molecular weight than the cut-off point of the membrane material are excluded.

15. An injection device for insertion into a patient comprising injection means for subcutaneous insertion, means for temporarily attaching the injection device to a patient and a chamber into which drugs or other injectable solutions may be inserted characterized in that the injection means is connected to the chamber by way of a semi-permeable membrane to prevent contaminated body fluids from leaking back to the chamber.

* * * * *